United States Patent
Tiquet et al.

(10) Patent No.: US 8,398,851 B2
(45) Date of Patent: Mar. 19, 2013

(54) METHOD OF DETERMINING THE FUEL CONTENT IN A COMBUSTION ENGINE LUBRICATING OIL

(75) Inventors: Laurent Tiquet, Gallardon (FR); Pierrick Rouille, Nanterre (FR)

(73) Assignee: Renault S.A.S., Boulogne Billancourt (FR)

(*) Notice: Subject to any disclaimer, the term of this patent is extended or adjusted under 35 U.S.C. 154(b) by 392 days.

(21) Appl. No.: 12/668,335

(22) PCT Filed: Jul. 7, 2008

(86) PCT No.: PCT/FR2008/051258
§ 371 (c)(1),
(2), (4) Date: Sep. 7, 2010

(87) PCT Pub. No.: WO2009/010678
PCT Pub. Date: Jan. 22, 2009

(65) Prior Publication Data
US 2011/0100092 A1    May 5, 2011

(30) Foreign Application Priority Data
Jul. 9, 2007   (FR) .................................... 07 04967

(51) Int. Cl.
*B01D 15/08* (2006.01)
(52) U.S. Cl. ............. 210/198.2; 210/656; 95/87; 95/88; 96/101; 96/102; 96/103; 96/105
(58) Field of Classification Search ................ 95/87, 88; 96/101, 102, 103, 105; 210/635, 656, 659, 210/198.2
See application file for complete search history.

(56) References Cited

U.S. PATENT DOCUMENTS

| | | | |
|---|---|---|---|
| 4,199,330 A * | 4/1980 | Nestrick et al. | 95/82 |
| 4,357,836 A | 11/1982 | Kokesh | |
| 5,250,093 A * | 10/1993 | Jiang et al. | 96/102 |
| 5,262,052 A * | 11/1993 | Rossiter et al. | 210/635 |
| 5,611,846 A | 3/1997 | Overton et al. | |
| 7,611,901 B2 * | 11/2009 | Fitamen et al. | 436/60 |
| 2002/0088753 A1 * | 7/2002 | Huber et al. | 210/656 |
| 2009/0029475 A1 * | 1/2009 | Fitamen et al. | 436/60 |

FOREIGN PATENT DOCUMENTS

FR    2892818 A1 *    5/2007

OTHER PUBLICATIONS

Anonymous: "Standard Test Method for Diesel Fuel Diluent in Used Diesel Engine Oils by Gas Chromatography", ASTM Designation, vol. D3524-4, pp. 1-6, XP009067885, (Nov. 11, 2004).
Abstract of French Patent No. 2,892,818.

* cited by examiner

*Primary Examiner* — Ernest G Therkorn
(74) *Attorney, Agent, or Firm* — Oblon, Spivak, McClelland, Maier & Neustadt, L.L.P.

(57) ABSTRACT

The invention relates to a device and to a method for determining the proportion of fuel in a combustion engine lubricating oil. The device according to the invention comprises a column (12) with at least 22000 theoretical plates and a steady state phase capable of separating the fuel, the oil, the internal standard contained in the oil and the solvent, in which the oil and the internal standard are diluted, and a heating module (120) capable of causing an increase in the temperature of the column (12) at a rate of at least 350° C./min. In the method according to the invention, the column (12) is subjected to determined cycles during which the pressure of the carrier gas and the temperature are varied.

8 Claims, 2 Drawing Sheets

METHOD OF DETERMINING THE FUEL CONTENT IN A COMBUSTION ENGINE LUBRICATING OIL

REFERENCE TO RELATED APPLICATIONS

This application is a 371 of PCT/FR2008/051258 filed Jul. 7, 2008.

The invention relates in general to the analysis of lubricating oils, and in particular the determination of the fuel content of an internal combustion engine oil.

In the context of the present invention, fuel means any type of fuel used in the operation of internal combustion engines, for example gasoline, diesel, biofuels, etc.

Methods for analyzing the fuel content (in particular of diesel) in a lubricating oil are known but are not fully satisfactory because they do not rapidly yield reliable, correct and accurate results.

In this field, a chromatograph is conventionally used like the one 10 shown in FIG. 1, which comprises an injector 11 of the products to be analyzed, a polymer 12 for separating the products to be analyzed flushed by a carrier gas which facilitates the elution of the compounds, a detector 13 of the said products. In operation, the separating column 12 is traversed at different speeds by the various compounds of the products to be analyzed. The detector 13 is for example a flame ionization detector known to the person skilled in the art and has a flame fed with gases issuing from the device 14. The detector 13 also receives a gas transporting products to the separating column, for example hydrogen, helium or nitrogen. The detector 13 measures a current generated during the combustion of a compound issuing from the column 12. The current generated varies according to the presence or absence of a compound in the chamber. A chromatogram is generated to represent, for example, the current as a function of time.

The use of such a chromatograph, known to a person skilled in the art, for determining the proportion of fuel (in particular diesel) in a lubricating oil, serves to obtain highly accurate analytical results. However, a method using such a chromatograph has the following drawbacks: on the one hand, a too slow temperature rise of the column, and on the other hand, a too long cooling time of the same column, thereby increasing the time of occupation of the chromatograph per sample.

The Applicant has developed a device for determining the proportion of fuel in an internal combustion engine lubricating oil, which remedies these drawbacks by using a chromatograph comprising a chromatography column in a particular heating module. The Applicant has also developed a method using such a device, in which the column is subjected to predefined cycles in which the carrier gas temperature and pressure in the column are varied, and which serves to obtain results that are reliable, correct and accurate.

More particularly, the present invention relates to a device for determining the proportion of fuel in an internal combustion engine lubricating oil, the lubricating oil containing an internal standard, and the lubricating oil and the internal standard being diluted in a solvent to form a mixture to be analyzed, the device comprising a gas phase chromatograph which comprises:

an injector of the products to be analyzed,
a separating column having an inside diameter $\Phi$, a length L and a stationary phase, said separating column being fed with carrier gas,
a heating module, and
a detector of said products, According to the invention, the separating column comprises at least 22000 theoretical plates, with a stationary phase present in the separating column in the form of a film at least 0.40 microns thick, this stationary phase being suitable for separating the internal standard, the solvent, the fuel and the lubricating oil. Also according to the invention, the heating module is suitable for causing an increase in the temperature of the column at a rate of at least 350° C./min.

Advantageously, the stationary phase is selected from methylpolysiloxanes.

The furnace in which the chromatography column is generally incorporated is replaced, in the inventive device, by a heating module generally located outside the furnace, which is advantageously a linear heating module which can be placed either along the column, or around it, for example in the form of a sleeve into which the column is inserted.

Such a heating module is suitable for faster increases and decreases in temperature than what is usually practiced, in particular with a chromatograph of which the separating column is a conventional furnace having a large volume, which generates high inertia in heating and in cooling, thereby causing a considerable reduction in analysis time.

Advantageously, a heating module is selected which is not only suitable for heating the column at a rate up to at least 350° C./min but which is also suitable for cooling it at a cooling rate that is at least equivalent.

If the heating module advantageously consists of a tubular heating resistor into which the column is inserted, it is possible to heat the column from ambient temperature to 350° C. at a rate of about 1000° C./min.

According to an advantageous embodiment of the invention, the column can be associated with a cooling device such as a fan or a refrigerating unit, which allows even faster cooling of the column, and particularly cooling from 350° C. to 30° C., in a time of 100 seconds or less.

The carrier gas in the separating column may be helium, hydrogen or nitrogen.

However, hydrogen is preferably used as carrier gas because it serves to obtain higher efficiency in terms of product separation.

According to a particularly advantageous embodiment of the present invention, the separating column of the chromatograph has an inside diameter $\Phi$ of 0.18 mm and a length of 10 m with a stationary phase thickness of 0.40 µm.

The present invention also relates to a method for determining the proportion of fuel in an internal combustion engine lubricating oil, using the device according to the invention. In the inventive method, the column (12) is subjected to a thermal cycle comprising the following successive steps:

A1) a holding plateau at an initial temperature $T_1$ between 20° C. and 40° C., to optimize the elution of the internal standard and the solvent from the start of the analysis t=0 s, comprising the dead time $t_0$, which is the time of passage through the column, for the compounds which are not retained by the stationary phase, and stopping at time $t_1$, which is generally shorter than the elution time of the internal standard and of the solvent from the detector;

A2) a temperature rise at a rate of at least 350° C./min from $t_1$ up to time $t_2$, which is the time required to optimize the separation of the $C_{20}$ hydrocarbon compounds of the fuel;

A3) a plateau at the temperature reached in step A2, from $t_2$ up to time $t_3$, which is the time required to optimize the separation of the $C_{25}$ hydrocarbon compounds of the oil and the lubricant;

A4) a temperature rise at the rate of at least 35° C./min, from $t_3$ up to the exit time $t_4$, which is the time required for all the hydrocarbon compounds of the oil to be detected, with a holding plateau at the final temperature Tf reached at $t_4$;

A5) cooling at a rate of at least 350° C./min to the initial temperature Ti of step A1, the type and thickness of the stationary phase having an influence on the durations of the various steps A1 to A5.

Advantageously, the column is simultaneously subjected to a carrier gas pressure variation cycle comprising the following successive steps:

during step A1 between $t_0$ and $t_1$, a plateau at an initial pressure $p_1$;

during step A2) between $t_1$ and $t_2$, a pressure increase $[p_1]$ to a pressure $p_2$ at a rate of at least 40 kPa/min;

during step A3) between $t_2$ and $t_3$, a plateau at pressure $p_2$;

during step A4) between $t_3$ and $t_4$, an increase in the pressure pat a rate of at least 30 kPa to a pressure $p_3$;

during step A5 after $t_4$, the pressure $p_3$ is lowered instantaneously to the initial pressure $p_1$;

the type and thickness of the stationary phase having an influence on the durations of the various steps A1 to A5 and the pressure values $P_1$ to $P_3$.

In the inventive method, the determination of the proportion of diesel in the oil comprises the following successive analytical steps:

the formation of a mixture containing a sample of lubricating oil to be analyzed and an internal standard compound (for example a $C_5$ hydrocarbon compound, which is not superimposed with the compounds to be analyzed) in a predefined proportion, the whole being diluted in a solvent (for example $CS_2$, which does not disturb the analysis), the injection of said mixture into the injector of chromatograph;

the establishment of a chromatogram of the sample to be analyzed;

the determination of a first parameter M representative of the area of a peak of the chromatogram associated with the internal standard compound ($C_5$ hydrocarbon compound) corrected for the mass really introduced into the mixture;

the determination of a second parameter C representative of the area of at least one peak of the chromatogram associated with a hydrocarbon compound representative of the diesel;

the determination of the proportion T of diesel in the sample to be analyzed by the formula:

$$T = \frac{C/(M) - b}{a}$$

Where:

a and b are constants defining the equation y=ax+b of a calibration line of the ratio between the second and the first parameter as a function of the proportion of diesel.

Advantageously, the second parameter C may be representative of the area of least one peak of the chromatogram associated with a $C_{20}$, $C_{21}$, $C_{22}$, $C_{23}$, $C_{24}$ or $C_{25}$ hydrocarbon compound, or of their sum total.

It may also be possible to previously calculate an approximation of the diesel content, by taking account of a second parameter which is only a function of the peak of the $C_{20}$ hydrocarbon compound. Depending on this approximation, one can then determine the peaks of the hydrocarbon compounds taken into account in parameter C, to calculate the diesel content. The number of peaks taken into account can thus be a function of the calculated approximation.

Advantageously, the second parameter may be representative of the area of several peaks associated with respective compounds selected from a group of ($C_{20}$-$C_{25}$) hydrocarbon compounds.

In order to take account of a relative area of the various compounds for various chromatographic conditions, the coefficient C is advantageously corrected to bring the concentration of the internal standard compound (C5) to a desired value. C may in particular be determined by the following formula:

$C = \alpha \cdot C_0/C_5$ $C_0$ is the area of the peak associated with the internal standard ($C_5$ hydrocarbon compound);

$\alpha$ is a correction factor toward a reference concentration, and $C_5$ is the concentration of the internal standard ($C_5$ hydrocarbon compound) in the sample.

The mixture formed may further comprise a predefined proportion of carbon disulfide $CS_2$. The carbon disulfide has the function of diluting the mixture of oil and $C_5$ hydrocarbon compound in order to mix them uniformly and to have a liquid and fluid medium which can be separated more easily. Furthermore, the carbon disulfide $CS_2$ is advantageously invisible to the detector, even in large quantities. The carbon disulfide therefore does not disturb the detection of diesel and oil. However, other solvents may be selected, provided that their signal in the final operation can be taken into account.

The calibration line is preferably obtained previously with the same type of diesel and the same type of oil as in the sample to be analyzed, in order to maximize the final accuracy.

For the prior determination of the equation of the calibration curve, the following steps can be carried out:

several standard mixtures are prepared comprising a lubricating oil and diesel in different predefined proportions, to which an internal standard (for example a $C_5$ hydrocarbon compound) is added in a predefined proportion and the whole is solubilized in the solvent $CS_2$.

The diesel content of the standard sample is denoted T0 below. For each standard mixture:

a standard mixture is injected into the injector of a gas phase chromatograph;

a chromatogram of the standard mixture is obtained;

a first parameter M0 is determined, representative of the area of a peak of the chromatogram associated with the internal standard ($C_5$ hydrocarbon compound);

a second parameter C0 is determined, representative of the area of a peak of the chromatogram associated with a diesel hydrocarbon compound representative of the diesel.

From the pairs of parameters obtained for the various mixtures obtained (which can be represented by points T0 on the x-axis and C0/M0 on the y-axis), the constants a and b of the calibration line are determined. The constants a and b are for example obtained by using as the calibration line, the line corresponding best to the various pairs formed (T0; C0/M0).

The chromatogram may be obtained by a flame ionization detector and in which a computation member makes integrations in order to calculate the area of each peak.

Other features and advantages of the invention will appear clearly from the description that follows, provided for information and nonlimiting, in conjunction with the appended drawings, in which:

DESCRIPTION OF THE PREFERRED EMBODIMENTS

The chromatograph of the prior art, and also its operating principle, have been described previously in the reference to the preceding prior art.

Figure 1:
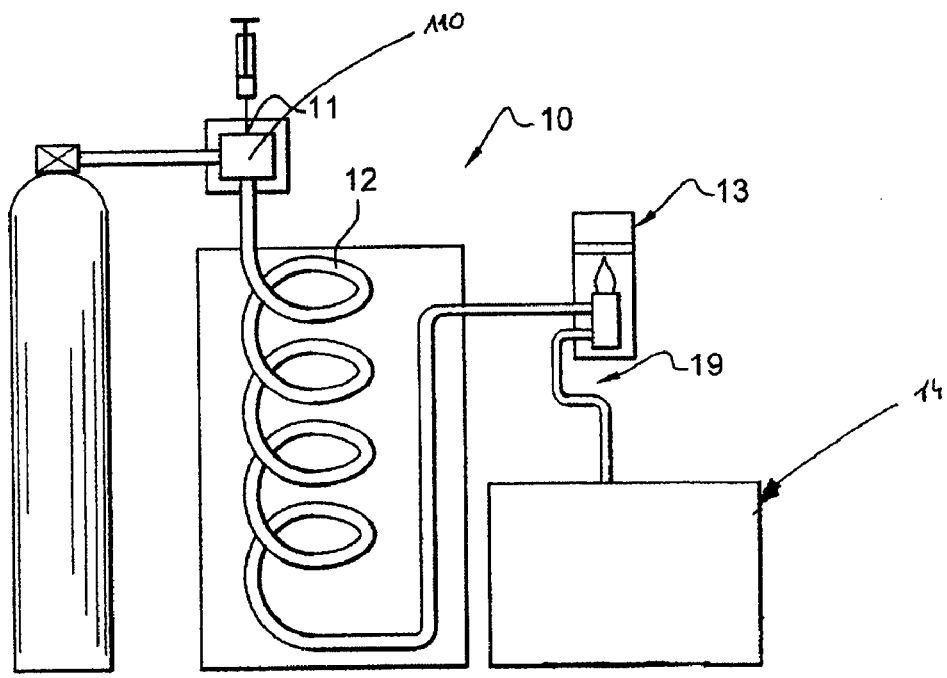
FIG. 1 schematically shows an example of a chromatograph according to the prior art.
Figure 2:
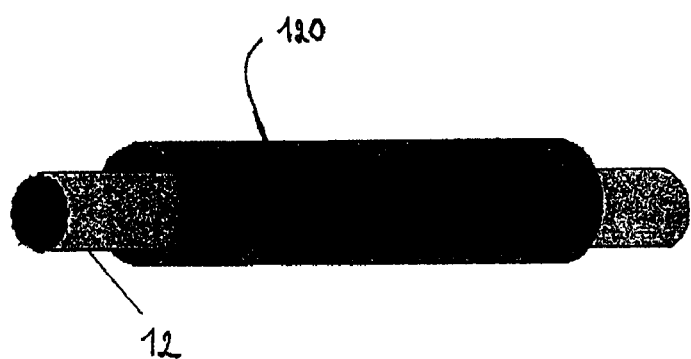
FIG. 2 schematically shows a separating column incorporated in a tubular heating module which is used to implement the inventive method, FIG. 3 schematically shows a device according to the invention comprising a chromatograph with the separating column shown in FIG. 2.

FIG. 2 shows a separating column 12 of the gas phase chromatograph used in the inventive method. This figure shows that the column 12 is integrated in a tubular heating module 120, which consists of a heating resistor.

Figure 3:
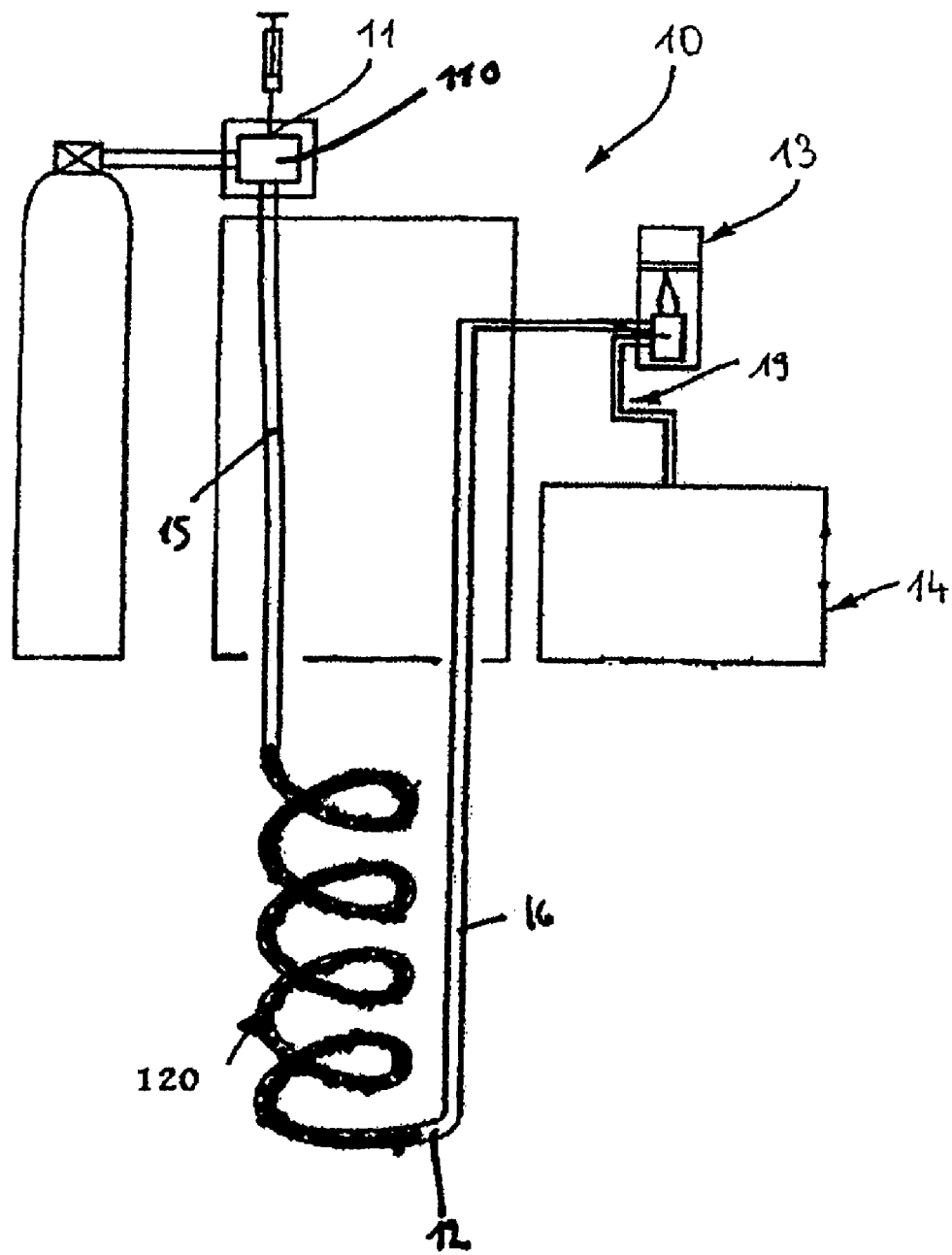

By now referring to FIG. 3, the apparatus used for the implementation of the inventive method comprises a gas phase chromatograph fed with hydrogen (for example grade N55) and having a precise programming and control of the temperature and pressure in the column. This chromatograph comprises:

an apolar capillary column 12 sold by RESTECH, which has a length of 10 meters and a diameter of 0.18 mm with a film thickness (stationary phase) of 0.4 µm; this column is incorporated in a tubular heating resistor 120;

a flow dividing injector 11 with pressure control and an injection controller having at least 8 positions, a 100-position passer being recommended;

a precolumn 15 devoid of phase connecting the injector 11 with the column 12, this precolumn having a length of 50 centimeters and being equipped with a union forming a junction with the capillary column 12;

a flame ionization detector 13 (FID);

a precolumn 16 devoid of phase connecting the detector 13 with the column 12, this precolumn being equipped with a union forming a junction with the capillary column 12;

an integration device in the form of a computer running the software sold under the reference HPCHEM in a minimal version at A.10.02;

a precision balance accurate to 0.1 mg;

a vibrating table for stirring and homogenizing the samples.

An example of the conditions of application of the inventive method, for taking measurements of the diesel content in various spent lubricating oils, is now described in detail.

For comparison, we have also taken measurements using an apparatus incorporating a chromatograph like the one shown in FIG. 2. The apparatus shown in FIG. 2 is different from the one in FIG. 3 in the use of an apolar capillary column having a length L of 10 m and a diameter of 0.53 mm with a film thickness of 1 µm, that is a ii)/L ratio of $5.3 \times 10^{-5}$. Use can be made for example of the apolar column sold by Chrompack/Varian under reference CP Syl 19cb. This column is integrated in a conventional furnace.

Reactants

For the implementation of the inventive method and that of the prior art method, the following reactants are used:

carbon disulfide $CS_2$ like the one sold by Prolabo with Normapur grade for analysis;

pentane ($C_5$) having a purity higher than 99%, commercial diesel;

new engine oil;

spent oils covering the entire concentration range targeted, for example from 0 to 10 wt % of diesel of this type.

Calibration of the Columns of Each of the Apparatus

Prior to the actual analytical phase, the columns of each apparatus are calibrated, the one used for the inventive method (shown in FIG. 3) and the one used for comparison using the prior art method (shown in FIG. 2).

This calibration is carried out similarly for both apparatus using standard samples (oil and diesel) of which the exact diesel content is known, and by correcting the internal standard (pentane).

To obtain good calibration accuracy, a new diesel and a new oil are used as standards, corresponding respectively to the diesel and the oil which have been used to obtain the samples for analysis.

For each standard sample, the following preparation steps are carried out:

the mass of oil in the sample corresponding to its mass assay is taken from a bottle and weighed; its mass is denoted $m_1$;

the volume of diesel required to obtain its mass assay is taken and placed in the bottle. The mass of oil-diesel mixture is denoted $m_2$;

the sample is shaken vigorously for at least 10 minutes with a vibrating table to homogenize it.

The standard samples are then subjected to the process described below for the samples to be analyzed.

The following samples are to be analyzed:

standard samples: E1, E2, E3, E4 each consisting of a mixture of new oil and diesel, samples of spent oils comprising estimated weight contents of diesel with regard to the weight of the sample, which are targeted in the desired range of concentrations to be analyzed.

For each of the oil samples to be analyzed E1 to E4, the following preparation steps are carried out in succession:

take about 1.5 g of sample and record the mass taken $m_3$,

40 µl of pentane (internal sample) are added to the sample to be analyzed; the pentane is stored and taken at ambient temperature and the mass of the mixture obtained (sample and pentane) is recorded $m_4$;

this mixture (sample+pentane) is virtually immediately diluted by adding solvent, 5 ml of carbon disulfide $CS_2$, the bottle containing the mixture obtained being sealed hermetically almost immediately in order to limit evaporation of the solvent $CS_2$;

the mixture obtained is stirred by a vibrating table for approximately 1 minute to homogenize the mixture. The mixture then obtained is thus diluted to 75% by volume in $CS_2$ and is ready for injection into the chromatograph;

optionally, to increase the shelf life of the mixture obtained, it is poured into a 2 ml microflask in order to guarantee a minimal dead volume (a hermetic plug can be crimped on the opening of the microflask) and as many microflasks are filled as required for a given mixture to be analyzed;

1 µl is injected by the automatic injector.

The quantities indicated above are obviously given for information, and other values can be used by the person skilled in the art.

The following was carried out for the four samples E1 to E4 and for the spent oils:

a chromatographic analysis by the inventive method, using the apparatus shown in FIG. 3, and a chromatographic analysis by the same method, except for the fact that instead of the apparatus in FIG. 3, an apparatus incorporating the chromatograph in FIG. 2 is used.

For the chromatographic analysis by the inventive method (using the apparatus in FIG. 3), the carrier gas in the separating column is hydrogen, and the column is subjected, from the deposition of a sample to be analyzed in the column, to the following thermal and hydrogen pressure variation cycles:

thermal cycle comprising successively:
a plateau of 24 at a temperature of 35° C.;
a temperature rise at 350° C./min to 230° C.;
a plateau at 230° C. for 45 s;
a temperature rise at 35° C./min to 310° C.;
a plateau at 310° C. for 120.6 s;
cooling from 310° C. to 30° C. in less than 100 s.

hydrogen pressure variation cycle comprising successively:
a plateau at a pressure of 40 kPa;
an increase of the hydrogen pressure from 40 kPa/min to 70 kPa;
a plateau at 70 kPa for 30 s;
an increase in the pressure from 70 kPa to 700 kPa at 30 kPa/min;
a plateau at 100 kPa for 153 s;
a decrease in the pressure from 100 kPa to 40 kPa.

For the chromatographic analysis by the prior art method using an apparatus incorporating the chromatograph in FIG. 2, the carrier gas in the separating column is helium and the column is subjected to the following thermal and variation cycles:

thermal cycle comprising successively:
a plateau of 5 min at a temperature of 35° C.;
a temperature rise at 6° C./min to 115° C.;
a temperature rise at 3° C./min to 177° C.;
a temperature rise at 2° C./min to 300° C.;
cooling from 310° C. to 30° C. in 20 min.

hydrogen pressure variation cycle comprising successively:
a plateau at a pressure of 24 kPa;
an increase in the hydrogen pressure at 1.5 kPa/min to 49 kPa;
an increase in the hydrogen pressure at 4 kPa/min to 100 kPa;
a plateau at 100 kPa;
a decrease in the pressure from 100 kPa to 24 kPa.

For this apparatus (shown respectively in FIG. 2), the temperature of the injector is controlled to follow a temperature program with an advance of 10° C., according to the oven track principle. The flow rate of carrier gas in the column is conditioned by the rate imposed by the helium pressure program and the chromatograph operates with pressure control. For the apparatus of said invention, the injector is of the flow divider type and the temperature of the injector is kept constant at 320° C.

For the two apparatus, the hydrogen flow rate in the detector is about 30 ml/min and the air flow rate in this detector is about 400 ml/min to the nearest 10 ml/min.

For integrating the peaks of the various compounds, the following periods were used in the chromatography cycle:

the internal standard portion (pentane) was integrated between t=22 seconds and t=33 seconds;

the integration of the carbon disulfide portion ($CS_2$) and the compounds of the diesel portion was carried out by excluding $C_{20}$, between t=33 seconds and t=37 minutes and 40 seconds, the excluded compounds between $C_5$ and $C_{20}$ belonging to the diesel;

the integration between the excluded compounds of the $C_{20}$ and $C_{22}$ diesel portion was carried out between t=37 minutes and 40 seconds and t=44 minutes and 15 seconds;

the integration between the compounds of the excluded $C_{22}$ and $C_{24}$ diesel portion was carried out between t=44 minutes and 15 seconds and t=51 minutes and 15 seconds;

the integration between the compounds of the excluded $C_{24}$ and $C_{25}$ diesel portion was carried out between t=51 minutes and 20 seconds and t=54 minutes and 20 seconds;

the integration of the oil portion from $C_{25}$ was carried out between t=54 minutes and 20 seconds and t=97 minutes.

Advantageously, the integration times of the various compounds are adjusted according to the aging of the column and controlled with the reference solution.

For the two analyses (by the inventive method and by the prior art method), the chromatograms obtained are analyzed to extract the areas of the peaks associated with the various compounds. Let A0 be the area extracted for the internal standard pentane, A1 being the area associated with carbon disulfide and at the start of the diesel to excluded $C_{20}$ where A2 is the area associated up to excluded $C_{22}$, A4 being the area associated up to excluded $C_{24}$ and A5 being the area associated up to excluded $C_{25}$.

Advantageously, the pentane standard concentration is brought to an imposed value. A relative area of the various compounds (or family of compounds), can thus be calculated, regardless of the chromatographic conditions.

The corrected area A0' is calculated as follows:

the mass of pentane is $m_4-m_3/m_4$.

let $[C_i]$ be the imposed concentration (for example 0.0066), so that: $A0'=A0*[C_i]/[C_5]$.

The calibration curve is plotted as follows for the two apparatus (that in FIG. 3 and the one incorporating the chromatograph in FIG. 2):

the weighed real diesel content is $g=(m_2-m_1)/m_2$;

for each area Ai, where is between 1 and 4, the line corresponding approximately to the function $$f(g) = \left(\sum_{k=1}^{i} Ak\right) \Big/ AO'$$

is plotted, for example by the least squares method.

By expressing the equation of the calibration line in the form $y = a_i x + b_i$, the values of $a_i$ and $b_i$ are determined. Four calibration lines are thus obtained from the same standards.

For a sample to be analyzed, the integrations are similarly made to determine the areas Ao', A1, A2, A3 and A4. For small between 1 and 4, the ratios $$\left(\sum_{k=1}^{i} Ak\right) \Big/ AO'$$

are then calculated.

From the ratios obtained and the calibration lines, the diesel content is determined by the following formula:

$$\left(\left(\left(\sum_{k=1}^{i} Ak\right) \Big/ AO'\right) - b_i\right) \Big/ a_i$$

If the lubricant is unknown, only the calculation of the diesel content for i=1 is taken into account.

For certain oils which are not superimposed with the heavy components of the diesel (having little co-elution between the two families of compounds), the result to be taken into account is determined according to the diesel content obtained for i=1. For example, if this value is between 0 and 2%, the value obtained for i=1 is taken into account; if this value is between and 10%, the value obtained for i=2 is taken into account; if this value is between 10 and 20%, the value for i=3 is taken into account; if this value is higher than 20%, the value for i=4 is taken into account. The co-elution of the diesel is then taken into account.

Certain oils may have a particular structure (for example if $C_{16}$ is present in the mixture), and a special integration may be required. Such an integration may in particular exclude the area of the peak corresponding to the compound concerned and require a specific calibration.

Advantageously, the temperature and pressure profiles on the chromatograph are corrected periodically according to standards prepared on a solution containing the $C_5$, $C_{20}$-$C_{26}$ and $C_{30}$ hydrocarbon compounds (with for example 60 mg of each of these compounds for 5 ml of $CS_2$). Thus the wear of the column and the change in retention times are thus taken into account.

Advantageously, new calibration lines are plotted for each placement of a new column in the chromatographs.

Results

The results of the analysis of the diesel content of samples E1 to E4 with, on the one hand, the inventive method (using the apparatus in FIG. 3) and on the other hand, the prior art method (using the chromatograph in FIG. 2) are given in Table 1.

time is six minutes and 30 seconds if the inventive method is used, instead of 2 hours with the prior art method, with the consequence that a single analysis is performed with the prior art method but eighteen analyses can be performed in the same time using the inventive method.

The invention claimed is:

1. A device for determining a proportion of fuel in an internal combustion engine lubricating oil, said lubricating oil containing an internal standard, and said lubricating oil and said internal standard being diluted in a solvent to form a mixture to be analyzed, said device comprising a gas phase chromatograph which comprises:

an injector of the products to be analyzed, a separating column having an inside diameter Φ, a length L and a stationary phase, said separating column being fed with carrier gas, a heating module, and a detector of said products, said separating column comprises at least 22000 theoretical plates, the stationary phase, which is in the separating column in the form of a film of at least 0.40 μm, is suitable for separating said internal standard, said solvent, said fuel and said lubricating oil, said heating module is suitable for causing an increase in the temperature of the column to at least 310° C. at a rate of at least 350° C./min.

2. The device as claimed in claim 1, wherein the stationary phase is selected from methylpolysiloxanes.

3. The device as claimed in claim 1, wherein said heating module is suitable for causing a cooling of the column at a rate of at least 350° C./min.

4. The device as claimed in claim 1, wherein the heating module is a linear module placed along or around said column.

5. The device as claimed in claim 4, wherein the heating module is a tubular heating resistor, in which the column is inserted.

6. The device as claimed in claim 5, wherein the column is associated with a fan or a refrigerating unit.

7. The device as claimed in claim 1, wherein the carrier gas is hydrogen.

8. The device as claimed in claim 1, wherein the column has an inside diameter Φ of 0.18 mm and a length of 10 m with

TABLE 1

|  | E1 | E2 | E3 | E4 | Number of analyses performed in two hours | Duration of the analysis in minutes |
|---|---|---|---|---|---|---|
| Prior art method | 2.05 ± 0.31% | 9.94 ± 0.54% | 5.05 ± 0.45% | 8.13 ± 0.52% | 1 | 120 |
| Inventive method | 2.20 ± 0.19% | 10.11 ± 0.80% | 4.76 ± 0.38% | 8.67 ± 0.65% | 18 | 6.5 |

Table 1 shows that using the "MURDIGA" inventive method, it is possible to obtain results as reliable and accurate as with the prior art method, and to obtain them more rapidly. In fact, for equivalent reliability and accuracy, the analytical a stationary phase thickness of 0.40 μm, and in that said column is fed with hydrogen.

\* \* \* \* \*